United States Patent
Ahlmén et al.

(10) Patent No.: US 8,459,262 B2
(45) Date of Patent: Jun. 11, 2013

(54) MANUAL VENTILATION WITH ELECTRONICALLY CONTROLLED APL VALVE

(75) Inventors: Christer Ahlmén, Sollentuna (SE); Pär Emtell, Vällingby (SE); Petter Videbrink, Upplands Väsby (SE); Kin-Chun Wong, Sundbyberg (SE); Mikael Kock, Åkersberga (SE)

(73) Assignee: Maquet Critical Care AB, Solna (SE)

( * ) Notice: Subject to any disclaimer, the term of this patent is extended or adjusted under 35 U.S.C. 154(b) by 1052 days.

(21) Appl. No.: 12/158,626

(22) PCT Filed: Dec. 21, 2006

(86) PCT No.: PCT/EP2006/070068
§ 371 (c)(1),
(2), (4) Date: Nov. 12, 2008

(87) PCT Pub. No.: WO2007/071756
PCT Pub. Date: Jun. 28, 2007

(65) Prior Publication Data
US 2009/0277448 A1    Nov. 12, 2009

Related U.S. Application Data

(60) Provisional application No. 60/597,836, filed on Dec. 21, 2005.

(51) Int. Cl.
*A61M 16/00* (2006.01)

(52) U.S. Cl.
USPC ............ 128/205.13; 128/200.24; 128/204.18; 128/204.21; 128/204.23; 128/205.14; 128/205.17

(58) Field of Classification Search
USPC ............. 128/204.21, 204.23, 200.24, 204.18, 128/205.13–205.14, 205.17
See application file for complete search history.

(56) References Cited

U.S. PATENT DOCUMENTS
5,471,979 A    12/1995    Psaros et al.

(Continued)

FOREIGN PATENT DOCUMENTS
| EP | 0 621 049 A1 | 10/1994 |
| EP | 0 769 304 A1 | 4/1997 |
| WO | WO 2004/067055 A2 | 8/2004 |

*Primary Examiner* — Loan Thanh
*Assistant Examiner* — Bradley Philips
(74) *Attorney, Agent, or Firm* — Schiff Hardin LLP

(57) ABSTRACT

A breathing apparatus for ventilating the lungs of a patient with breathing gas, has: a breathing circuit configuration; a mechanical ventilation system; a manual ventilation system provided with a manual ventilation bag; a manual ventilation valve for enabling manual ventilation of breathing gas from the breathing circuit; a pressure sensor devised to detect the pressure level in the breathing circuit; an electronically controlled expiration valve (40) that in a mechanical ventilation mode is controlled to control the pressure level in the breathing circuit according to a first set of predetermined control rules adapted to mechanical ventilation mode requirements; said electronically controlled expiration valve in a manual ventilation mode being coupled to enable ventilation of breathing gas from the breathing circuit by means of the manual ventilation system according to a second set of predetermined control rules adapted to manual ventilation mode requirements. In a method for controlling a breathing apparatus, an electronic expiration valve is controlled during the mechanical ventilation mode as well as during the manual ventilation mode of the apparatus. The control of the expiration valve can be implemented by means of a software product for the breathing apparatus embodying programming instructions as control rules, which, when executed in the apparatus, enable control of the expiration valve during manual ventilation.

33 Claims, 7 Drawing Sheets

U.S. PATENT DOCUMENTS

| | | | |
|---|---|---|---|
| 5,497,767 A * | 3/1996 | Olsson et al. | 128/205.13 |
| 6,651,657 B1 | 11/2003 | Manigel et al. | |
| 7,992,555 B2 * | 8/2011 | Heinonen et al. | 128/204.21 |
| 2001/0029946 A1 * | 10/2001 | Kitten | 128/203.14 |

\* cited by examiner

MANUAL VENTILATION WITH ELECTRONICALLY CONTROLLED APL VALVE

RELATED APPLICATION

The present application claims the benefit of U.S. provisional application 60/597,836, filed Dec. 21, 2005.

BACKGROUND OF THE INVENTION

1. Field of the Invention

The present invention relates in general to ventilation systems in breathing apparatuses, such as anesthesia apparatuses, and in particular to a ventilation system with a mechanical ventilation system combined with a manual ventilation system. The invention provides a breathing apparatus and also a method for controlling a breathing apparatus, especially an electronic expiration valve in the apparatus. The invention also concerns software products for controlling a breathing apparatus.

2. Background and Prior art

When patients are subjected to anesthesia there is usually a transition from ventilation by spontaneous breath, via a phase of manually controlled ventilation by means of a manual breathing bag over to mechanically controlled ventilation, and vice versa when the patient is taken out of anesthesia. A direct transition from spontaneous to mechanical ventilation is considered to be too harsh for the patient and it is important to closely monitor the patient's response to the anesthesia. A human operator executing manually controlled ventilation with a direct contact between the breathing bag and the lungs of the patient is more sensitive to the conditions and the reactions of the patient than the mechanical ventilation system and can adjust anesthesia parameters in a smoother and safer way. Also during mechanical ventilation operators sometimes want to switch over to a phase of manually controlled ventilation in order to check the condition of the patient, for example in connection with a change in the composition of an anesthetic gas or in connection with distribution of an anesthetic agent.

Anesthesia apparatuses are therefore usually provided with a manual ventilation system in parallel with an automatic mechanical ventilation system, and a ventilation selection switch for selecting between the manual and the mechanical ventilation system. Although having tubing, valves and other components in common in a breathing circuit connected to the lungs of a patient, the manual and the mechanical ventilation systems are basically separate systems with separate pressure control valves designed for different purposes and functions.

In the manual ventilation system an important control valve is the adjustable pressure limit valve, commonly called APL valve. The APL valve has the function to limit the pressure of breathing gas that can occur in the breathing circuit during manual ventilation. Traditionally, the APL valve is provided with a spring that exerts pressure on a diaphragm that seals off a vent passage against a valve seat. When the pressure exceeds the spring force, the APL valve opens to vent excess gas into an evacuation system. The valve is adjusted by compressing the spring with a screw mechanism so that the level of the compressed spring force corresponds to the wanted pressure limit.

FIG. 2A-FIG. 2C show schematically pressure and flow characteristics in a breathing circuit, with a prior art APL valve drawn as graphs of pressure and flow parameters over time in an exemplifying case of operation. FIG. 2A shows the system pressure in the breathing circuit Psys over time t, with the indicated level APL that is preset on the adjustable pressure limit valve. FIG. 2B shows the compression rate of the manual bag over time t, which for example would correspond to or can be described as the change rate in the volume of the manual bag (time derivative of bag volume). FIG. 2C shows the flow of gas Qout over time that is let out from the system in this instance via the APL valve. FIG. 2C also shows the flow Qpat over time to and from the patient. In FIG. 2C, the flow level Qf is the flow level of the fresh gas flow, which usually is a selectable and adjustable constant flow. Thus, in the time interval from 0 to T1 the patient inspires a part Qpat of the fresh gas flow Qf and the rest of the fresh gas flow builds up the pressure Psys until the APL pressure level is attained at T1. At T1 the APL valve opens and lets out a gas flow corresponding to the fresh gas flow level Qf, and at the same time the flow to the patient ceases. The manual bag is now filled at the APL pressure level. At T2 the operator compresses the manual bag which results in an increase in the flow Qout from the breathing circuit since the APL pressure level is already attained. No gas flow to the patient is induced by the bag compression from T2 to T4, which rather has the purpose of adjusting the volume in the manual bag by pressing out superfluous fresh gas from it. At T4 the compression of the manual bag is also released and the patient starts an expiration phase that lasts until T5. At T5 an inspiration phase begins. At T6 the operator starts manual bag compression and induces an increased gas flow Qpat to the patient until T7. At T7 the APL pressure is attained whereupon the flow Qpat to the patient ceases and the outlet pressure Qout starts and lasts until T8. At T8 the manual bag compression is released and the patient starts an expiration phase that lasts until T9 during which the outlet flow Qout ceases and the manual bag is filled with the gas expired from the patient. In FIG. 2C the changes in the flow curves Qpat and Qout coincide at T1 and T7, respectively, but for visibility reasons the flow curves are drawn with a gap in between.

Another valve type commonly used in manual ventilation is the Berner valve described in U.S. Pat. No. 3,780,760. FIG. 3A-3C show in a similar way the characteristics of such a prior art Berner valve. FIG. 3A shows the system pressure in the breathing circuit Psys over time t, with the indicated level PBern that is preset on the Berner valve for a pressure level to be maintained as long as there is no compression of the manual bag. FIG. 3B shows the compression rate of the manual bag over time t. FIG. 3C shows the flow of gas Qout over time that is let out from the system in this instance via the Berner valve. FIG. 3C also shows the flow Qpat over time to and from the patient. In FIG. 2C, the flow level of the fresh gas flow is indicated as Qf. Thus, in the time interval from 0 the patient inspires a part Qpat of the fresh gas flow Qf until the Psys attains the PBern pressure level, whereupon the Berner valve opens and lets out a flow Qpat. The flow to the patient ceases until T1 where compression of the manual bag starts and the Berner valve is mechanically triggered to allow a pressure that exceeds the PBern pressure level. From T1 to T2 a relatively high flow Qpat flows to the patient and from T2 it decreases to and remains at the lower fresh gas flow level Qf as the operator holds the manual bag at a constant volume until T3. At T3 the operator releases the bag compression and an expiration phase is started, which results in a flow Qpat from the patient to the manual bag followed by an increase up to Qf level in the outlet flow Qout from the breathing circuit. In FIG. 3C the indicated area between the curves Qout and Qpat corresponds to the gas volume in the bag. At T5 the pressure level PBern is attained and maintained until T6. At T6 the manual bag is compressed, this time to less degree than the previous compression, and again the pressure Psys increases and there is again a two step first high then lower flow Qpat to the patient. At T8 an expiration phase starts and proceeds with the same pattern as before. With such a Berner valve, there is a risk that the pressure increases to a too high a level with an entailing risk for injuries on the patient, such as barotraumas. Further, if the fresh gas flow Qf exceeds a mechanical trigger level, there is that the fresh gas flow Qf is mistakenly interpreted as a breath.

When the mechanical ventilation mode is set, the APL valve or the Berner valve is no longer a part of the breathing circuit. The mechanical ventilation system operates, in the absence of the APL valve or corresponding valve, with an expiration valve for venting excess gas into the evacuation system. In prior art breathing apparatuses the expiration valve is electronically controlled not only to limit the maximum pressure that should occur in the breathing circuit but also to ensure a minimum pressure in the breathing circuit. This minimum pressure is commonly known as the positive end expiratory pressure PEEP and is important to ensure that the lungs of a patient always to some extent are filled with breathing gas in order not to collapse and be completely deflated. The expiration valve is therefore usually called a PEEP valve. The PEEP valve is flexibly operated via the normal user interface of the breathing apparatus and is usually controlled by means of a control computer program realizing a set of predetermined rules adapted to the requirements of the mechanical ventilation mode.

The manual ventilation system of such breathing apparatuses is less flexible and does not allow for very accurate control of the pressure in the breathing circuit. There is therefore a need for improvements in the manual ventilation system of breathing apparatuses having both a manual and an automatic mechanical ventilation system.

There are different examples of prior art showing breathing apparatuses with manual and mechanical ventilation systems.

WO 2004/067055 A2 shows an example of an open ventilation system of the type described above with a manual ventilation system, an automatic mechanical ventilation system and a ventilation selection switch to select between the manual and the mechanical systems. This piece of prior art is directed to such a ventilation system in which the number of components that must be autoclaved are reduced. The use of a $CO_2$ absorber, an APL valve or Berner valve is eliminated. A selection valve for connecting either of the manual or the mechanical ventilation system is provided outside the patient circle. The gases from the patient are prevented from returning to the manual bag in order to eliminate the need for autoclaving the manual bag. The automatic mechanical ventilation system and the manual ventilation system have separate expiration valves for the outlet of exhalation gas to atmosphere.

In the manual ventilation mode fresh inhalation gas is input to the manual bag via a bag filling valve that is devised with an adjustable bias spring in order to allow a gas flow to the bag dependent on a differential pressure between the inhalation gas source and the manual bag. This bag filling valve has the function to limit the pressure in the manual bag. When the manual bag is manually compressed breathing gas flows via an inhalation conduit through a patient input branch of a Y-piece connected to the airways of the patient. In the exhalation phase, exhalation gas from the patient flows through a patient output branch of the Y-piece via an expiration valve selector that in the manual ventilation mode is open for evacuation of exhalation gas through a manual expiration valve to atmosphere. The maximum pressure of the manual bag is controlled independently of the pressure in the airways of the patient and exhalation gas is simply let out through the manual ventilation expiration valve, and therefore there is no need for an APL valve or a Berner valve in this piece of prior art.

In the mechanical ventilation mode, fresh inhalation gas flows past the manual bag branch, which is closed by means of the ventilation selection switch, to the patient via the Y-piece in the same manner. In the exhalation phase, exhalation gas flows via the expiration valve selector that in the mechanical ventilation mode is open for evacuation of exhalation gas through an automatic ventilation expiration valve. A separately controlled automatic ventilation mode PEEP valve is provided in the mechanical ventilation system.

U.S. Pat. No. 5,471,979 discloses an example of a breathing circuit that is coupled in a circle system and arranged for re-use of anesthetic gases that are not absorbed by the patient. This piece of prior art shows an entirely mechanical ventilation system and there is neither any manual bag nor any APL valve.

SUMMARY OF THE INVENTION

An object of the present invention is to improve the manual ventilation system of a breathing apparatus having a manual ventilation system and an automatic mechanical ventilation system.

There are the following aspects of the problem:
  To enable a more accurate and flexible control of the manual expiration valve function.
  To enable remote control of the manual expiration valve function.
  To achieve a simpler and less costly breathing apparatus.
  To improve the pressure conditions in the manual bag under certain breathing gas flow conditions,
  To enable realization of different modes of valve characteristics.

According to the present invention the problem is solved by coupling, in a manual ventilation mode, the manual ventilation system to the electronically controlled expiration valve of a mechanical ventilation system so as to control the pressure in the breathing circuit during manual ventilation. The electrically controlled expiration valve is controlled according to a set of predetermined control rules that are adapted to manual ventilation mode requirements. The mechanical APL or Berner valve of prior art manual ventilation systems is thus substituted by the expiration valve of the automatic ventilation system and a specific manual ventilation mode expiration control device. The invention provides an improved control of the manual expiration valve function and thereby also achieves a higher level of patient safety since a high pressure level can be maintained with more accuracy. So, for example, the risk for barotraumas that exists with a Berner valve is eliminated. Thus, the number of complex/expensive valves are reduced compared to the prior art. The inventive concept also provides a method for controlling a breathing apparatus wherein an electronic expiration valve is controlled during the mechanical ventilation mode as well as during the manual ventilation mode of the apparatus. The control of the expiration valve can be implemented by means of a software product for the breathing apparatus comprising control rules, which when executed in the apparatus enable control of the expiration valve during manual ventilation.

The invention enables the realization of different and adjustable pressure and flow characteristics of the breathing circuit by controlling the expiration valve in accordance with selectable schemes embodied in the control rules. This has the further effect that manual ventilation valves can be eliminated from the breathing apparatus. According to a further aspect, the invention enables remote control of the manual expiration valve function.

The invention makes it possible to maintain a certain adjustable pressure in the manual bag in the manual ventilation mode. This improves the tactile properties of the manual bag since the operator can adjust the pressure such that he has a convenient palpable contact with the lungs of the patient via the manual bag.

DESCRIPTION OF THE PREFERRED EMBODIMENTS

Figure 5:
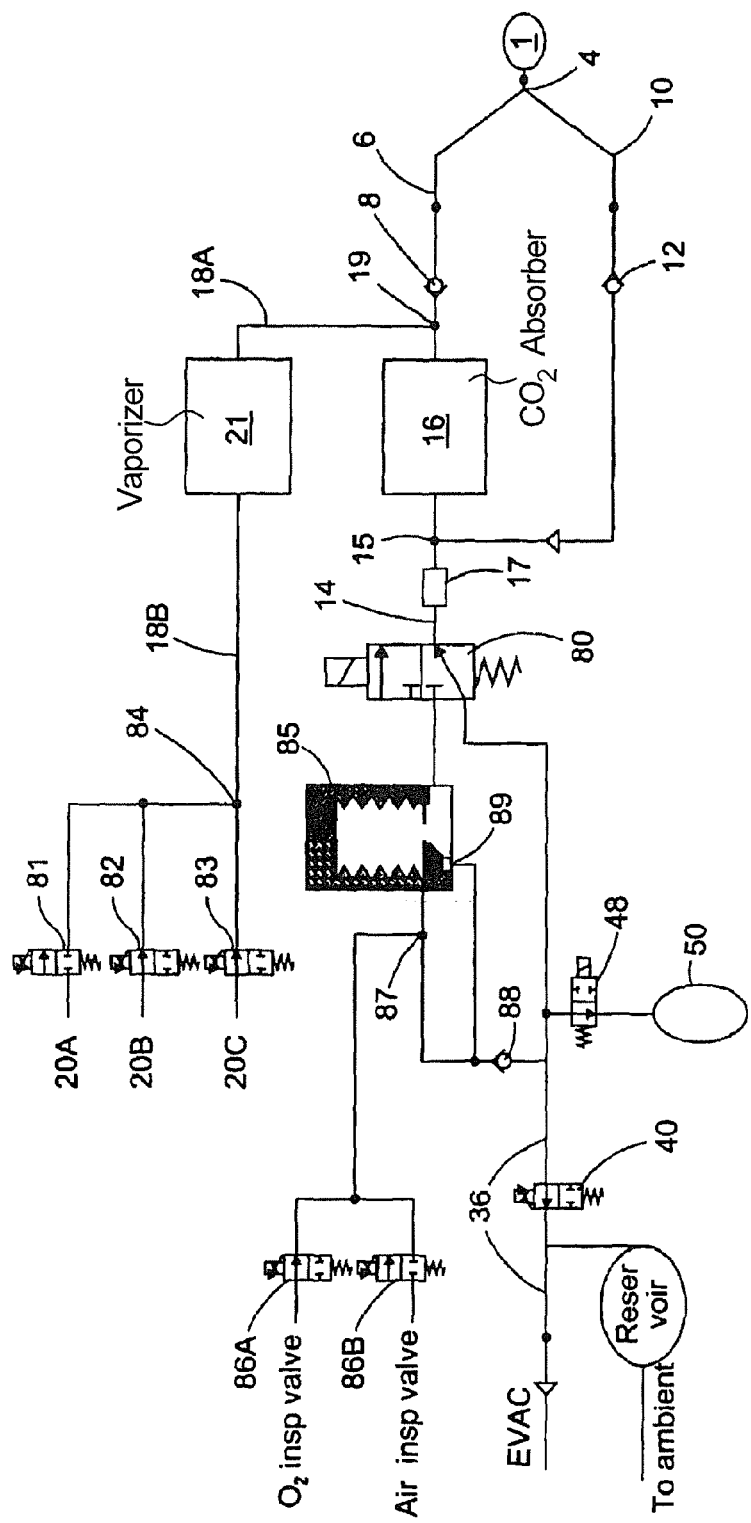
FIG. 5 shows a schematic drawing of a ventilation system, in accordance with embodiments of the invention.
Figure 6:
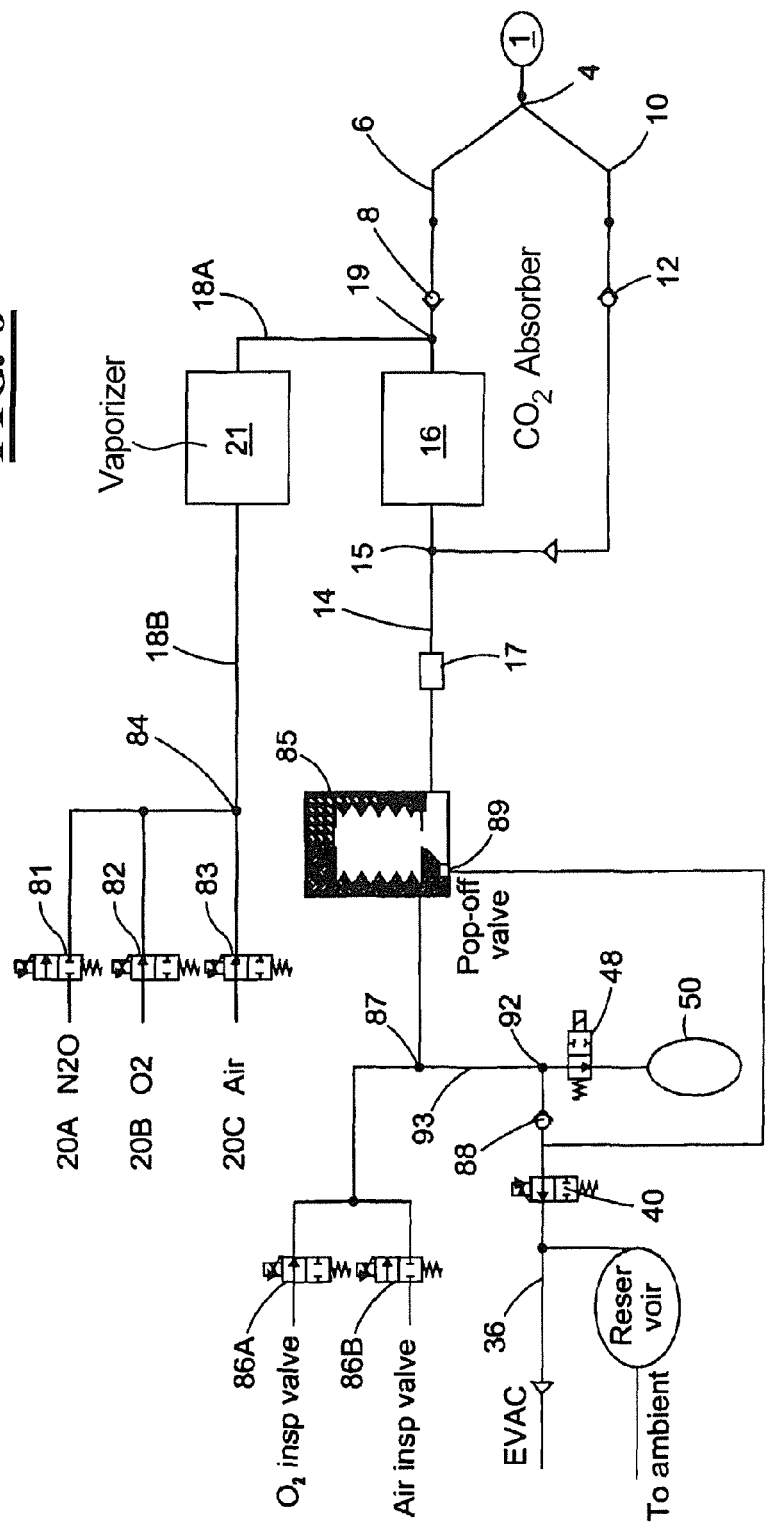
FIG. 6 shows a schematic drawing of a ventilation system, in accordance with embodiments of the invention.
Figure 7:
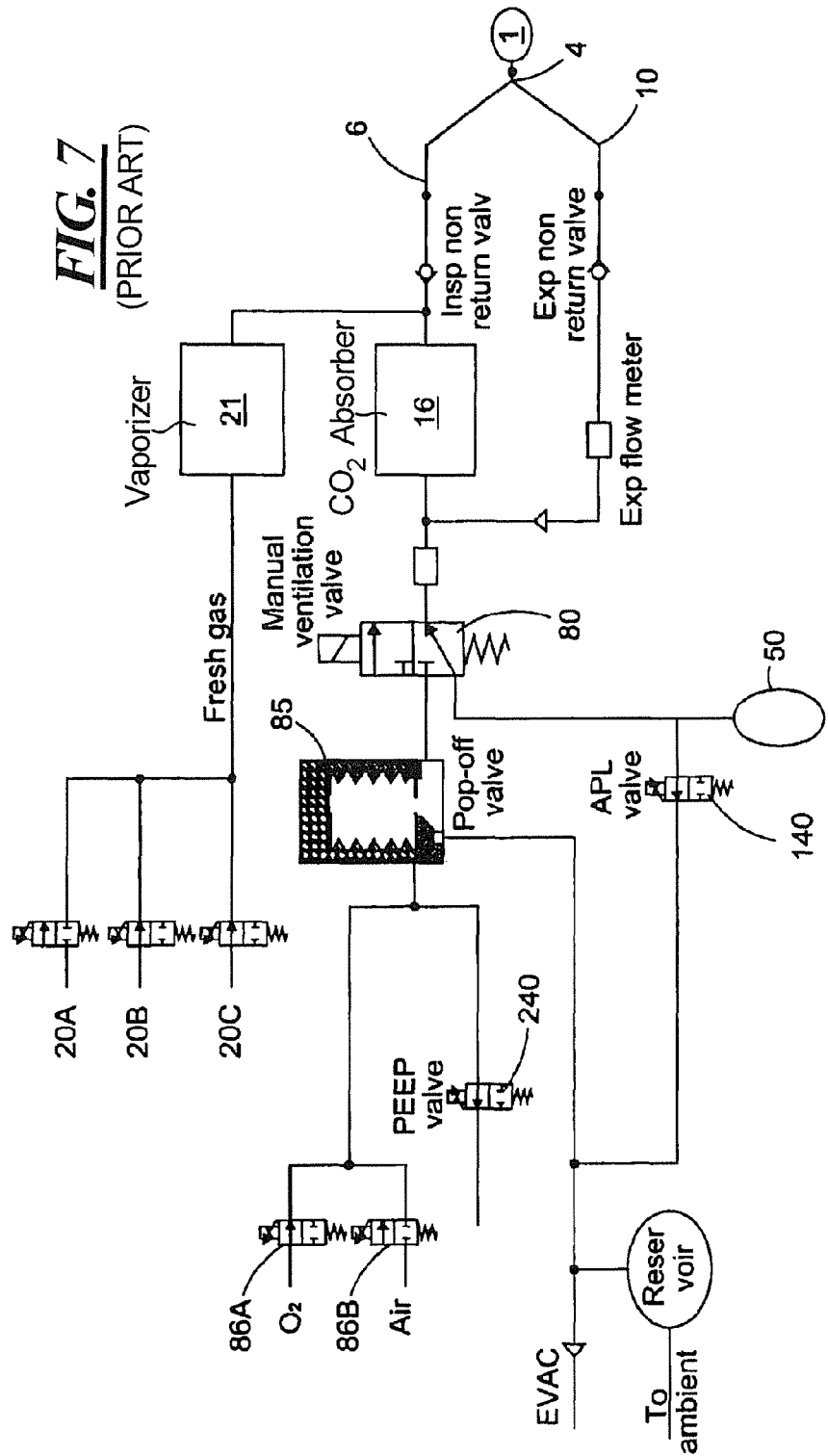
FIG. 7 shows a schematic drawing of a ventilation system, accordance to prior art.

To illustrate the differences between the invention, especially the embodiments in FIGS. 5 and 6, and prior art FIG. 7 illustrates a known configuration. The configuration in FIG. 7 includes a mechanical and a manual ventilation system that selectively by means of a manual ventilation valve 80 can drive breathing gas in a breathing circuit. The breathing circuit includes a patient 1 connector to a $CO_2$-absorber 16, one way valves, and the circle is connected to the manual ventilation valve and also to a vaporizer 21 by means of which fresh gas from gas supply units 20A-C can be supplied to the circle.

During mechanical ventilation, driving gas is supplied from gas sources through selection valves 86A, B to a bag in bottle unit 85 driving breathing gas inside the bag to and from the breathing circle, via the manual ventilation valve 80. The pressure of the breathing gas is controlled during expiration in that the driving gas flow through a PEEP valve 240. Excess gas, in the breathing circuit, is released through a POP-off valve in the bag in the bag-and-bottle unit 85, and further to an evacuation system.

During manual ventilation a manual bag 50 is used to drive breathing gas to and from the patient via the manual ventilation 80 valve and the patient circle. An APL-valve 140 is arranged limiting the pressure from the bag, said APL-valve is a mechanical valve, comprising a manually adjustable turning knob and a spring loaded valve. Excess gas is released through the APL-valve to an evacuation system.

Figure 1:
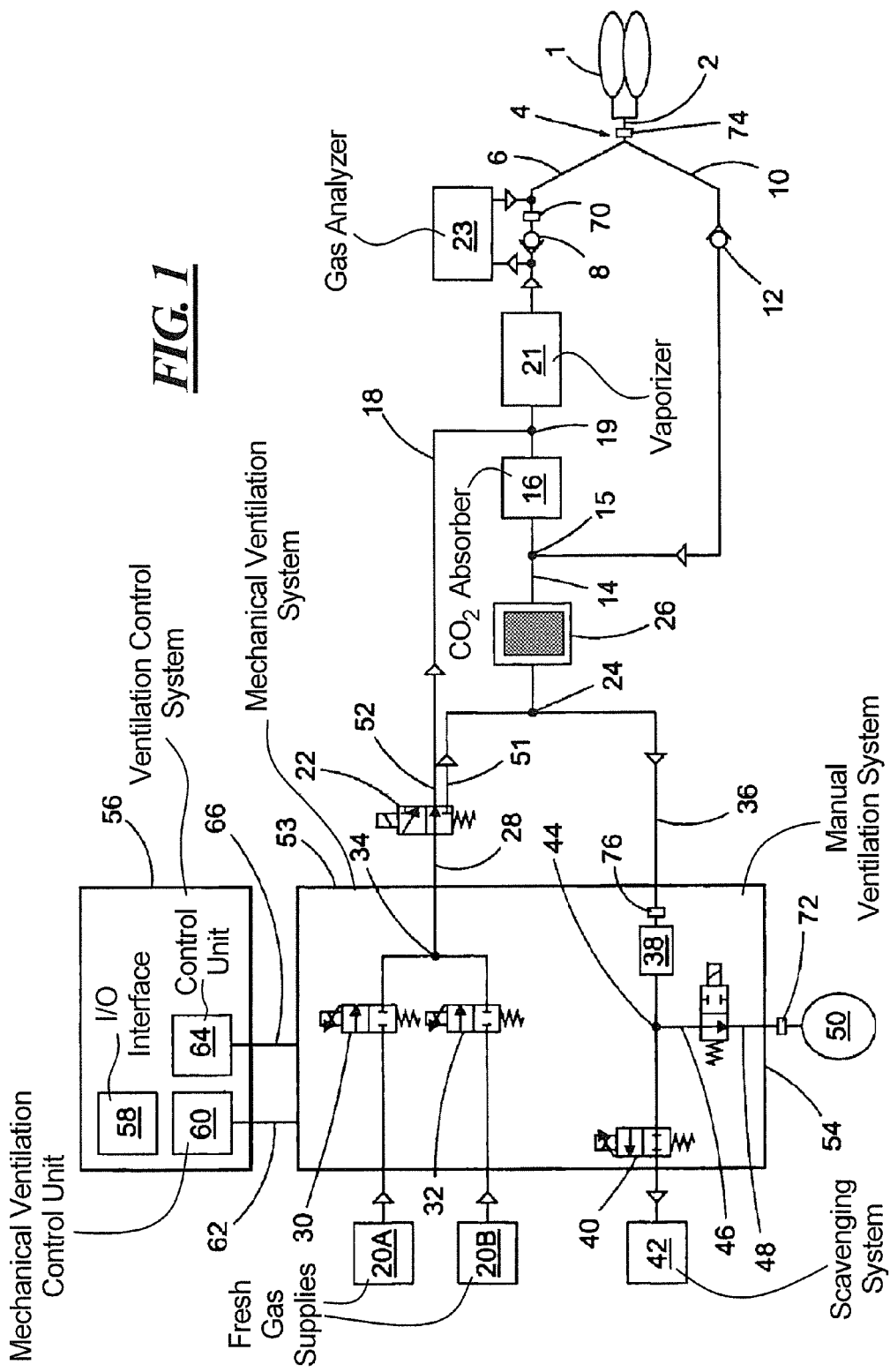
FIG. 1 shows a schematic drawing of a ventilation system, in accordance with embodiments of the invention.

FIG. 1 shows schematically, a breathing circuit coupled in a circle system with a mechanical ventilation system 53 and a manual ventilation system 54 configured in accordance with embodiments of the present invention The airways of a patient 1 are connected to a patient branch line 2 of a Y-piece 4 in a circular tubing system with an inspiration branch line 6 provided with a one-way inspiratory valve 8 and an expiration branch line 10 provided with an one-way expiratory valve 12. In one embodiment a pressure sensor 74 is provided in the patient branch line of the Y-piece 4. After the one-way expiratory valve 12, in a clockwise direction along the circle system, there is a common expiration and inspiration line 14 for the delivery of inspiration gas to the patient and evacuation of expiration gas from the patient coupled to the breathing circle at a junction 15. Further along the circle system the tubing passes through a $CO_2$ absorber 16 and after the absorber there is gas supply branch line 18 provided to feed fresh inhalation gas into the circle system from a fresh inhalation gas source 20A, 20B and coupled to the breathing circle at a junction 19. After the junction 19 there is a vaporizer 21 devised for vaporizing gas components in the flow of inspiration gas to the patient. In the exemplifying breathing circuit the vaporizer should be an injection type vaporizer in order to work properly with the mechanical ventilation system as well as with the manual ventilation system. A gas analyzer 23 is provided to analyze gas contents with an input of sample gas just before the one-way inspiratory valve 8 and an output of the sample gas just after the one-way inspiratory valve 8. A pressure sensor 70 is provided between the one-way inspiratory valve 8 and the output of the sample gas The common expiration and inspiration line 14 is provided with an adsorption filter 26 devised for adsorption and desorption of anesthetic and respiration gases to or from the patient.

At the distal side (from the perspective of the patient) of the adsorption filter 26 the common expiration and inspiration line 14 is coupled at a junction 24 to a first output branch line 52 from a selection valve 22, here in the shape of a bypass valve. A second output branch 52 of the selection valve 22 is coupled to the fresh gas supply line 18. At an input side, the selection valve 22 is coupled to an input line 28 leading from the fresh inhalation gas source 20A, 20B. The selection valve 22 is devised to select the flow route for the fresh inhalation gas via the supply branch line 18 or via the common expiration and inspiration line 14 passed the adsorption filter 26 into the breathing circle.

In this example there are two different gases in the inhalation gas source, more specifically Oxygen $O_2$ in the inhalation gas source 20A which is coupled to an $O_2$ inspiration valve 30 that in its turn is connected to the selection valve input line 28 at a junction 34. Similarly, there is Nitrous oxide $N_2O$ in the inhalation gas source 20B which is coupled to an $N_2O$ inspiration valve 32 that also is coupled to the selection valve input line 28 at the junction 34. The $O_2$ inspiration valve 30 and the $N_2O$ inspiration valve 32 are devised for adjusting the inlet flow and the proportions of the respective gases into the input line 28. Only $O_2$ and $N_2O$ are shown, but air can also be used as is common in the art.

In the embodiment of the invention shown in FIG. 1 the selection valve is a bypass valve 22 which has the function of selecting fresh inhalation gas flow either through the first output branch 51 or through the second output branch 52 of the selection valve 22. Thus, with the selection valve being actuated to a first flow selection mode the fresh inhalation gas is enabled to flow to the patient via the common expiration and inspiration line 14 and through the adsorption filter 26, or via the supply branch line 18 then bypassing the adsorption filter 26 as well as the $CO_2$ absorber 16.

An evacuation line 36 is connected to the common expiration and inspiration line 14 and to the mentioned first output branch line 52 at the junction 24. The evacuation line 36 leads via a flow meter 38 and a pressure sensor 76 to an expiration valve 40 that is devised to control output of evacuated gas flow from the breathing system to a scavenging system 42 or to the atmosphere. A manual ventilation line 46 is connected to the evacuation line 36 at a junction 44. The manual ventilation line 46 is provided with a manual ventilation valve 48 and leads to a manual bag 50 devised for manual ventilation. In one embodiment there is a pressure sensor 72 provided on the manual bag side of the manual ventilation valve 48.

The mechanical ventilation system 53 and the expiration valve 40 as well as other components are preferably parts of a per se known mechanical ventilator with a ventilation control system 56. The ventilation control system 56 comprises a user input/output interface 58 with command input means and display means of a per se known type. In a further development of the invention, the interface may also be provided with remote control means for remote control of the manual expiration valve functions or characteristics. The remote control function may for example be realized in a per se known manner as shown in EP1426966, where an anesthetic machine is provided with remote control for controlling alarms and transitions between mechanical ventilation and manual ventilation.

Also in a per se known manner, the ventilation control system 56 comprises mechanical ventilation control means 60 usually comprising specifically designed computer program code for controlling the operation of the mechanical ventilation system 53 and its components via a symbolically shown control line 62. The mechanical ventilation control means 60 enables vent of breathing gas from the mechanical ventilation system according to a first set of predetermined control rules for controlling the expiration valve 40 in accordance with mechanical ventilation mode requirements. In effect, the expiration valve is in this connection controlled to open or close at predefined pressure levels that occur in the tubing system. Typically the control rules realize pressure control functions such as a PEEP valve function and the like. Usually a PEEP valve is closed during inspiration and controls the pressure level, and flow, during expiration.

The ventilation control system 56 further comprises a manual ventilation control means 64. The a manual ventilation control means 64 is devised to control the expiration valve 40 via the symbolically shown control line 66 according to a second set of predetermined control rules and enable mechanical ventilation features adapted to manual ventilation mode requirements.

In the manual ventilation mode, the manual ventilation valve 48 is actuated to an open position in order to allow gas flow in the manual ventilation line 46 to and from the manual ventilation bag 50, and the manual ventilation control means 64 is activated to control the expiration valve 40. The effect of this is that the same expiration valve 40 is used for the manual ventilation system as well as for the mechanical ventilation system, but is controlled according to different sets of control rules. Switching over from mechanical to manual ventilation mode, and vice versa, involves actuating the manual ventilation valve 48 to enable the selected ventilation mode as well as selecting the corresponding ventilation control mode on the user input/output interface 58 of the ventilation control system 56. When the manual ventilation control mode is selected on the ventilation control system 56, the mechanical ventilation mode functions for the expiration valve 40 are disabled.

The manual ventilation control mode is in different embodiments adapted to different manual ventilation mode requirements. For this purpose the manual ventilation control means 64 comprises different subsets of predetermined manual ventilation control rules.

In one embodiment, the manual ventilation control rules are adapted to control the expiration valve (40) to keep a standby pressure level Pstb in the tubing system of the breathing circuit, in order to maintain a predetermined degree of gas volume content in the manual bag. The idea is to keep the manual bag filled with breathing gas to such an extent and with such a pressure that there is a palpable contact with the gas pressure in the lungs of the patient from the manual bag as it is operated by a human operator. In this control mode it is enabled that the patient can breathe spontaneously to and from the manual bag, while excessive gas is let out via the expiration valve.

Figure 2A:
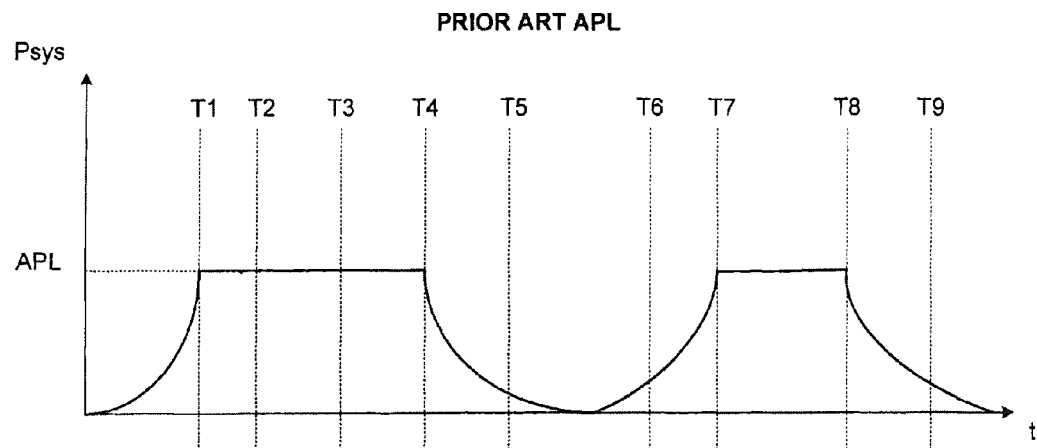
FIG. 2A to 2C show a schematic illustration of pressure and flow characteristics in a breathing circuit provided with a prior art APL valve.
Figure 2B:
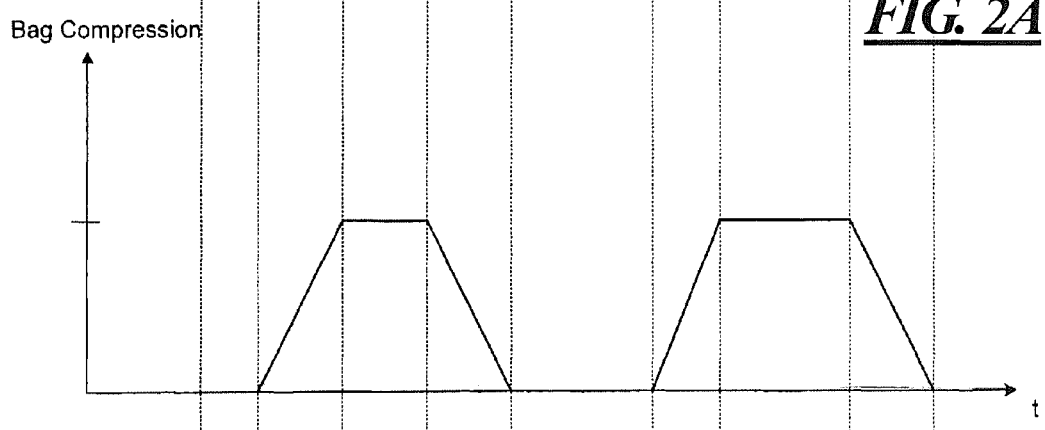
Figure 2C:
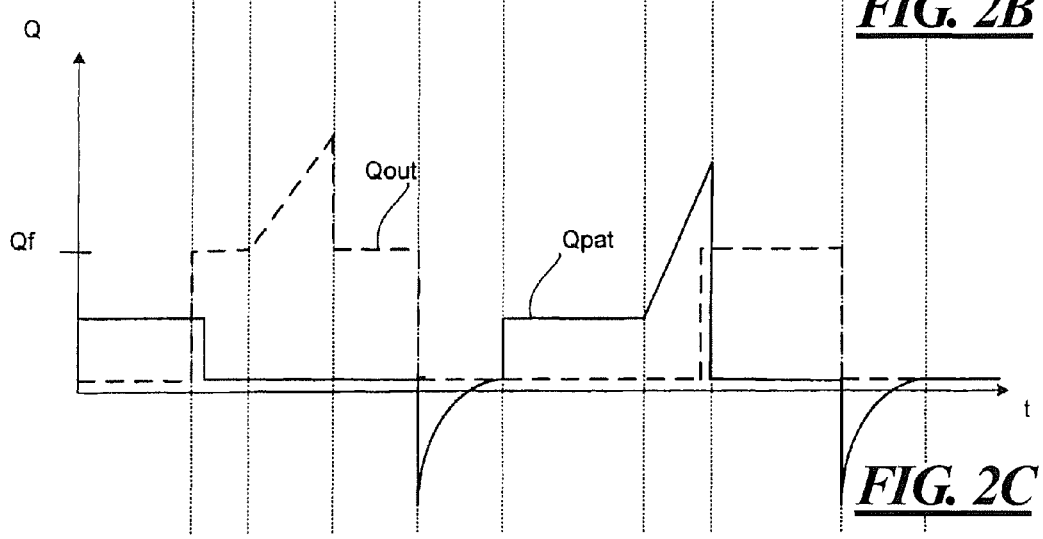
Figure 3A:
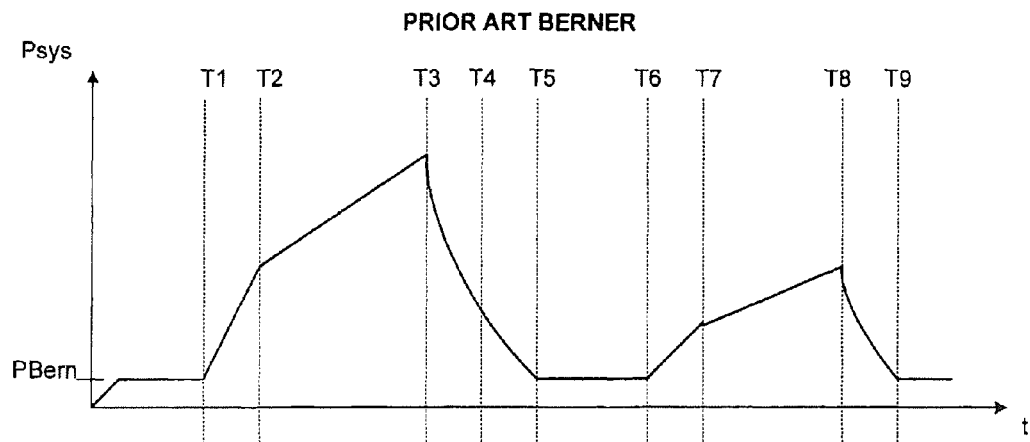
FIG. 3A to 3C show a schematic illustration of pressure and flow characteristics in a breathing circuit provided with a prior art Berner valve.
Figure 3B:
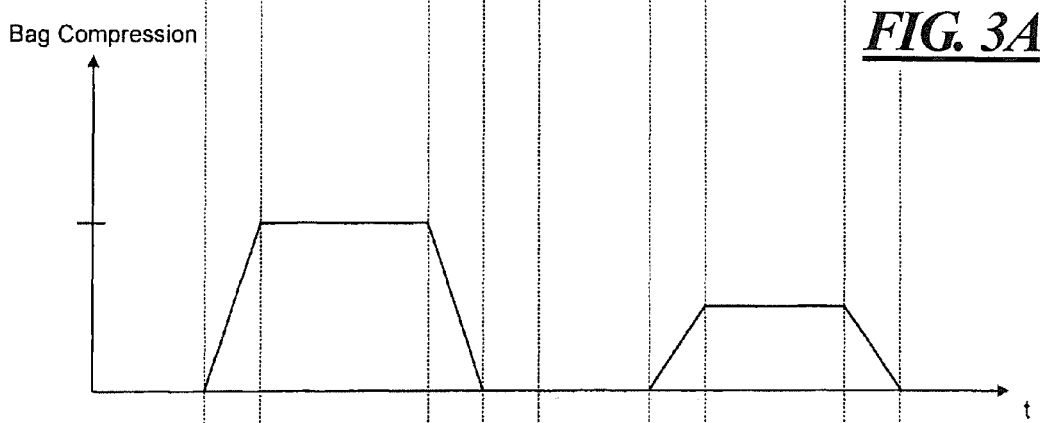
Figure 3C:
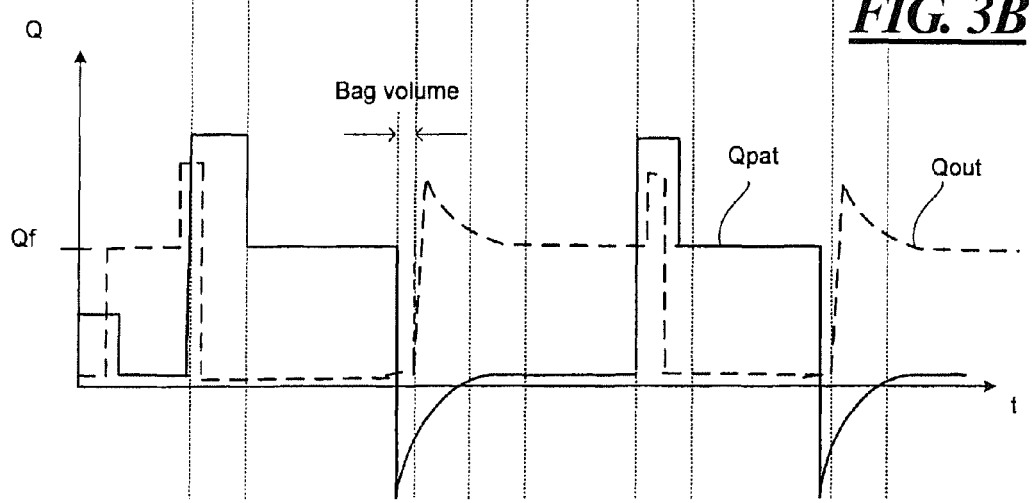
Figure 4A:
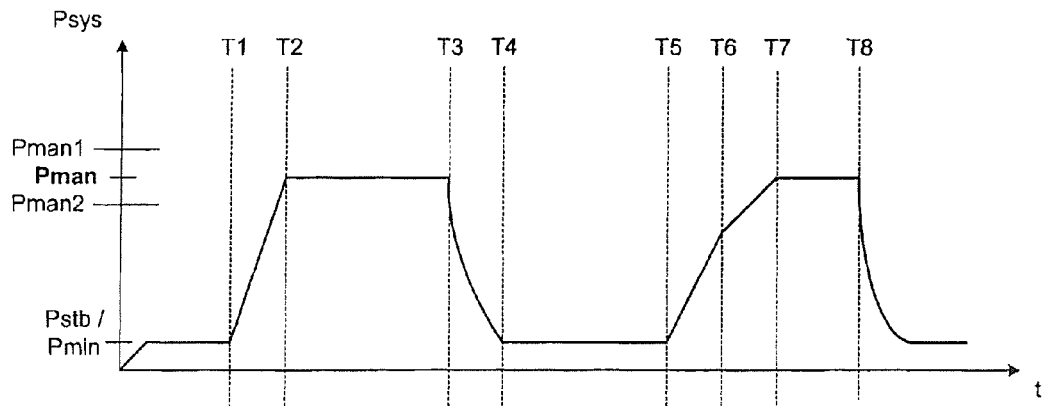
FIG. 4A to 4C show a schematic illustration of pressure and flow characteristics in a breathing circuit provided with an electronically controlled APL valve in accordance with embodiments of the invention.
Figure 4B:
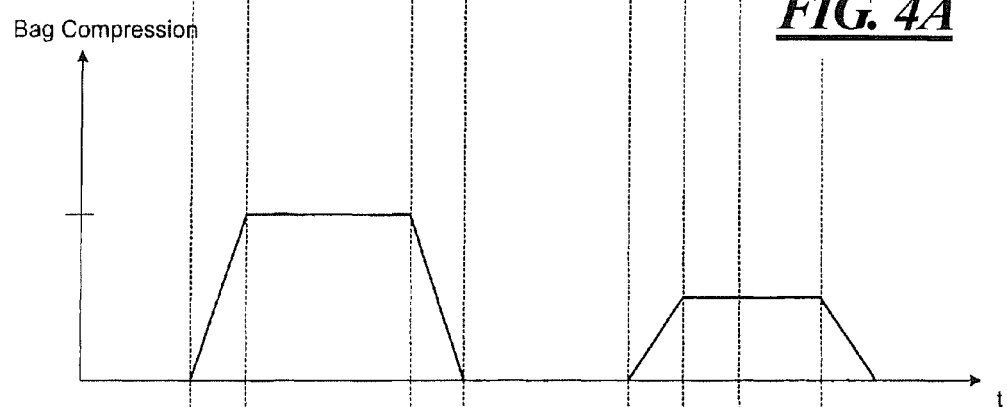
Figure 4C:
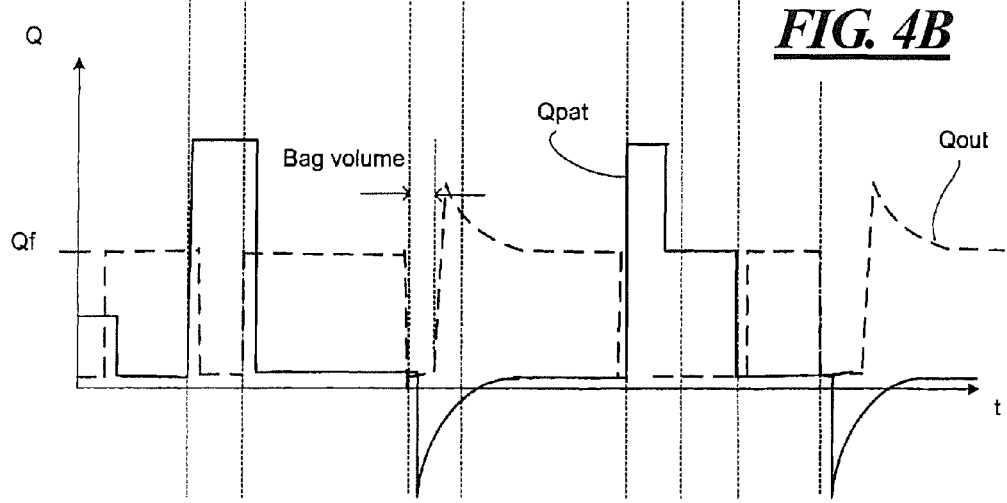

FIG. 4A-4C illustrates the characteristics of embodiments of the invention in a manner similar to that of the previously described FIGS. 2-3, and reference is made below to FIG. 4. As with the previously explained FIG. 2C the changes in the flow curves Qpat and Qout coincide at certain times, and similarly for visibility reasons the flow curves in FIG. 4C are drawn with a gap in between.

FIG. 4A-FIG. 4C show schematically pressure and flow characteristics in a breathing circuit, with an electronically controlled expiration valve operated in the manual control mode drawn as graphs of pressure and flow parameters over time in an exemplifying case of operation. FIG. 4A shows the system pressure in the breathing circuit Psys over time t, with the indicated pressure levels Pman, Pman1, Pman2, Pstb and Pmin that are devised to be preset by means of the manual ventilation control means. These pressure levels are explained below. FIG. 4B shows the compression rate of the manual bag over time t, which as described above for example would correspond to or can be described as the change rate in the volume of the manual bag, i.e. the time derivative of the bag volume. FIG. 4C shows the flow of gas Qout over time that is let out from the system in this instance via the APL valve. FIG. 4C also shows the flow Qpat over time to and from the patient. In FIG. 4C, the flow level Qf is the selectable and adjustable flow level of the fresh gas flow.

Thus, in the time interval from 0 the patient inspires a part Qpat of the fresh gas flow Qf until the Psys attains a first pressure level, which may be a standby pressure level Pstb or a minimum pressure level Pmin, whereupon the expiration valve 40 is opened to let out a flow Qpat. The flow to the patient ceases until T1 where compression of the manual bag starts.

Thus, when a manually induced breath shall be induced, the operator compresses the manual bag at time T1 such that the pressure and/or flow characteristics in the breathing circuit changes during the time interval T1 to T2, which is detected by the control system with the aid of a suitable sensor, for example pressure sensor 76 and/or flow meter 38. If the detected change in pressure and/or flow characteristics matches a predetermined first pattern, the expiration valve (40) is controlled to enable a predetermined maximum pressure level corresponding to a desired manual ventilation pressure level Pman in the breathing circuit. With the triggering event devised to be a quick compression of the manual bag, the predetermined first pattern of the pressure and/or flow characteristics in the breathing circuit would preferably comprise an increase in pressure corresponding to a predetermined pressure increase rate starting from a predetermined minimum pressure level that may correspond to the standby pressure level Pstb or some other selected minimum pressure level.

From T1 to T2 a relatively high flow Qpat flows to the patient and from T2 it ceases when the expiration valve 40 is opened for an outlet flow Qout corresponding to the fresh gas flow level Qf as the operator holds the manual bag at a constant volume until T3. The manual ventilation pressure level is typically higher than the standby pressure Pstb, and thus the expiration valve (40) is controlled to close until the manual ventilation level is attained at T2. The pressure in the breathing circuit then rises with the compression action on the manual bag until the manual ventilation pressure is attained at time T2 and the patient receives an induced breath. The expiration valve 40 is then controlled to keep the pressure at this level throughout the induced breath during the time interval from T2 to T3, and to open if the pressure level is exceeded. At T3 the operator releases the bag compression and an expiration phase is started, which results in a flow Qpat from the patient to the manual bag followed by an increase up to Qf level in the outlet flow Qout from the breathing circuit. In FIG. 4C the indicated area between the curves Qout and Qpat corresponds to the gas volume in the bag.

In this mode the manual ventilation control rules are thus further adapted to control the expiration valve (40) to allow a predetermined minimum pressure level in the breathing circuit Pmin. This minimum pressure level Pmin may coincide with the standby pressure level Pstb or may be a different selected level that in one embodiment is adjustable via a selection input means during manual ventilation. The purpose is, as described above, to enable a suitable pressure in the manual bag. When the induced breath is terminated at time T3, i.e. when the compression of the manual bag ends, the expiration valve is controlled such that the pressure in the tubing system returns to the predetermined minimum level at time T4. Thus, at T4 the pressure level Pstb/Pmin is attained and maintained until T5. The patient has an expiration phase during the time interval from T3 to T5, and as illustrated in FIG. 4 the operator gives at T6 a following manually induced breath with less bag compression during the time interval T5 to T8. Again the pressure Psys increases and there is again a two step first high then lower flow Qpat to the patient. The operator can in this mode thus continue to give manually assisted breathing by compressing the manual bag while maintaining a certain pressure in the breathing circuit as well as in the manual bag.

When expiration phases start and the manually induced inspiration ends at time T3 and T8 respectively, the expiration valve is controlled to open or close such that the pressure in the breathing circle returns to the standby pressure level. This is preferably achieved such that the second set of predetermined control rules are adapted to control the expiration valve (40) to attain the predetermined standby pressure level Pstb in response to a detected predetermined second pattern of the pressure and/or flow characteristics in the breathing circuit. This predetermined second pattern preferably comprises a decrease in pressure corresponding to a predetermined pressure decrease rate that occurs when the operator releases the manual bag at time T3 and T8 and the bag is allowed expand.

In one embodiment the inventive concept is implemented to realize an APL (Adjustable Pressure Limit) valve that operates with two different pressure levels as described above. The second set of predetermined control rules are in this embodiment adapted to control the expiration valve (40) to enable and attain a predetermined first, high pressure level Pman in the breathing circuit in response to a detected predetermined first pattern of the pressure and/or flow characteristics in the breathing circuit that occurs when an operator starts to compress the manual bag. Similarly, the second set of predetermined control rules are adapted to control the expiration valve (40) to enable a second, lower pressure level Pmin that is above the atmospheric pressure in response to a detected predetermined second pattern of the pressure and/or flow characteristics in the breathing circuit that occurs when the operator releases the compression of the manual bag. This thus has the effect that the operator of the breathing apparatus can switch between the lower and the higher pressure levels by compressing and releasing the manual bag, respectively.

In a further developed variety the second set of predetermined control rules are adapted to control the expiration valve (40) to enable pressure variations in the breathing circuit around the first and/or second pressure levels within predetermined pressure variation intervals, for example between Pman1 and Pman2 as illustrated in FIG. 4A. With a suitable selection of pressure variation intervals above and below the respective first and/or second pressure level(s), this variety has the effect that the patient is enabled to breathe spontaneously at the higher pressure as well as at the lower pressure.

The second set of predetermined control rules are preferably further adapted to control the expiration valve (40) to allow a predetermined maximum pressure level in the breathing circuit in response to a command signal received from a command signal input means. In this control mode there is no minimum pressure level higher than the atmosphere and the pressure and/or flow characteristics are thus similar to that of a breathing circuit provided with a traditional APL valve as described in above with reference to FIG. 3.

The invention enables a flexible selection of valve control modes. A general embodiment is devised such that the second set of predetermined control rules are adapted to control the expiration valve (40) to enable predetermined pressure characteristics that depend on detected pressure and/or flow characteristics in response to a command signal received from a command signal input means. For example, the control rules can be adapted such that the predetermined pressure characteristics correspond to those of a Berner valve as described in above with reference to FIG. 3.

In a further embodiment, the control means are devised to trigger a change from a mechanical ventilation mode to a manual ventilation mode in response to a detected change in pressure and/or flow characteristics that matches a predetermined pattern, for example a certain pressure change rate. The effect of this is that an operator can trigger the change from a mechanical ventilation mode to a manual ventilation mode for example by means of a quick compression of the manual bag that results in a first pattern of the pressure and/or flow characteristics in the breathing circuit detected by the control means, enter into a manual ventilation mode and proceed with manual ventilation. The return from the manual ventilation mode to the mechanical ventilation mode may be triggered for example in response to a detected predetermined time interval without any detected significant pressure changes in the manual bag that similarly results in a second pattern of the pressure and/or flow characteristics in the breathing circuit detected by the control means. Pressure changes in the manual bag that occur during the time interval and that are not to be taken for manual ventilation action can for example come from the operator touching or tactilely test compressing the manual bag for diagnostic purposes. Another origin of non-triggering pressure changes may be the spontaneous breathing of the patient. It is also enabled that the patient can breath spontaneously into the manual bag, and it is not necessary to ventilate mechanically during parts of the process of anaesthetizing or awakening the patient. For these purposes a pressure sensor 72 is provided close to or in the manual bag, since when the breathing apparatus is set in the mechanical ventilation mode the manual ventilation valve 48 is closed and other pressure sensors in the system are not possible to use for detecting pressure conditions of the manual bag.

The invention can for example be realized by providing a per se known ventilator 52 with an existing expiration valve 40 with computer program code for realizing the manual ventilation control means 64, and with the tubing connected to a circle system and a manual bag via a manual ventilation valve 48 as described above.

Two different configurations of a breathing apparatus, in the form of anesthetic machines, where the invention is implemented, are shown in FIGS. 5 and 6, respectively. The pressure in the breathing circuits in FIGS. 5 and 6 is controlled in accordance with the first and second set of rules as described above and in the claims below.

The patient breathing circle is the same in the different configurations shown in FIGS. 5 and 6, comprising an inspiration and an expiration branch, respectively. As in the apparatus in FIG. 1 there is a patient Y-piece 4 for a patient connected to an inspiration branch line 6 and an expiration branch line 10. In the expiratory flow direction, from the Y-piece, the expiration branch line includes a one-way valve 12 and is further connected to a junction 15 connecting the expiration branch line to a common inspiration and expiration line 14, and also to the inspiration branch line 6. The inspiration branch line is provided with, in the inspiratory flow direction starting from the junction 15, a carbon dioxide absorber 16, a junction 19, a one-way inspiration valve 8 and further connected to the Y-piece for the patient. Junction 19 connects the inspiration branch line (and the breathing circle) to a vaporizer 21 via a fresh gas branch line 18A. The vaporizer is further connected via branch line 18B to gas sources 20A, 20B and 20C, supplying air, $O_2$ and $N_2O$, so that in the flow direction the fresh gas supply sources is connected via the vaporizer to the breathing circle at junction 19, between the carbon dioxide absorber 16 and the inspiratory one-way valve 8. The gas sources 20A-C is connected, or disconnected, by means of supply valves 81, 82, 83, for $N_2O$, $O_2$ and air, to the fresh gas supply line 18A via a junction 84. To supply anesthetics to the breathing circle and further to the patient one, or at least one, of the gas sources supply gas via its respective supply valve 81-83 to the vaporizer and further to the breathing circle and to the patient as is common in anesthesia machines. These configurations can also include a gas analyzer, for example in the inspiration branch, and include pressure sensors at Y-piece and in the evacuation line as described in connection to FIG. 1. The common inspiration and expiration line 14 is, in the embodiments, provided with a flow meter 17.

The configurations in FIGS. 5 and 6 differ in the driving of the breathing gas in the patient breathing circle, but both configurations include a common expiration valve 40 for manual and mechanical ventilation in an evacuating line 36. This expiration valve 40 is used to control the pressure level in expiration and inspiration branch of the patient breathing circle. The same expiration valve 40 is used by the manual ventilation as well as by the mechanical ventilation system, but is controlled according to different first and second sets of control rules.

Both implementations have a "bag in bottle" 85 to drive the breathing gas in the patient circle. This bag in bottle 85 is, as is usual, provided with a, so called, pop-off valve 89, releasing excess gas from the breathing circuit to an evacuation system. In FIG. 5 the driving gas in the mechanical ventilation system is provided to the outside side of the bag in bottle. The expiration valve 40 controls the pressure of the driving gas by regulating the flow of the driving gas through the expiration valve to evacuation, and the pressure in the breathing circle is controlled by the pressure of the drive gas by means of the bag in bottle. Gas sources ($O_2$ and air) are connected via respective supply valves 86A, 86B and further to a junction 87 connecting the gas sources to the bag in bottle 85 and the expiration valve 40 via a one-way valve 88 and a junction 89. In this way the gas sources provide driving gas, during mechanical ventilation, to the bag driving the breathing gas inside the bag and which driving gas pressure is adjusted by, means of controlling, the expiration valve 40. The manual ventilation bag 50 is connected to the evacuation line 36 including the expiration valve 40 via the junction 90. Between the bag and the junction 90 is provided a manual ventilation valve 48 for selecting manual ventilation. The junction 90 connects the manual ventilation bag 50 to the expiration branch 36 with the expiration valve 40 and to the breathing circle via a selection valve 80 and the common inspiration and expiration line 14. Thus the expiration valve 40 controls the pressure provided by the manual bag 50 to the breathing gas flow in the breathing circuit. The selection valve 80 arranged in the common inspiration and expiration line 14 selectively connects the bag in the bag in bottle 85 and the manual ventilation bag 50 to the breathing gas circle. Thus, the manual ventilation system, driven by the manual bag, is connected to the breathing circle providing gas flow to and from the circle and excess gas through expiration valve 40 controlling the pressure by controlling the flow of breathing gas, or supplied fresh gas to the breathing circuit.

In FIG. 6 both the manual ventilation system and mechanical ventilation system drive the breathing gas by providing driving gas on the outside of the bag in the bag in bottle, and thus driving the breathing gas inside the bag to and from the breathing circle. In FIG. 6 the gas sources, that provide driving gas, are also connected via respective supply valves 86A, 86B to the outside of the bag in the bag in bottle, via a junction 87 that also connects the driving gas to the expiration valve 40 via a one-way valve 88, similar to the apparatus in FIG. 5. The manual system is arranged different since the manual bag is arranged to provide driving gas, supplied from the gas sources, to the outside of the bag in the bag in bottle. As shown in FIG. 6 the manual bag is connected to the bag via junction 92 to driving gas line between junction 87 and one-way valve 88.

The control rules are different in the mechanical mode and in the manual mode, the expiration valve is the same. The breathing apparatuses in FIGS. 1, 5 and 6 adjust the pressure level in the breathing circuit according to these rules, by controlling the electronic expiration valve 40. FIG. 1 illustrates control means 60, 64 in the control system 56 that controls the expiration valve. The apparatuses in FIGS. 5 and 6 suitably also includes control means, for example including a control unit such as a computer, to adjust the expiration valve, but this control unit is not shown in the Figs.

Thus, the ventilator in FIGS. 5 and 6 also include a ventilation control system comprising means for controlling mechanical and manual ventilation and a user input/output interface with command input means and display means of a per se known type. The ventilation control system comprises computer program code for controlling the operation of the mechanical ventilation and manual ventilation, enables the electronic expiration valve to open or close at pre-defined pressure levels and thereby limit the pressure in the breathing circuit, according to a first set of predetermined control rules during mechanical ventilation mode, controlling pressure such as a PEEP valve function, and according to a second set of predetermined control rules during manual ventilation enabling and adapting mechanical ventilation features for manual ventilation mode requirements.

The configurations include the manual ventilation valve 48, the opening of which allow gas to flow to the manual ventilation bag 50 (via line 46) and activates the manual ventilation mode and, thus, activating the control of the electronic expiration valve 40 in accordance with the second set of rules adapted for manual ventilation requirements. As in FIG. 1 the same expiration valve 40 is used for the manual ventilation system as well as for the mechanical ventilation system, but is controlled according to different sets of control rules. Switching over from mechanical to manual ventilation mode, and vice versa, involves actuating the manual ventilation valve 48 to enable the selected ventilation mode as well as selecting the corresponding ventilation control mode on the user input/output interface of the ventilation control system. When the manual ventilation control mode is selected on the ventilation control system, the mechanical ventilation mode functions for the expiration valve 40 are disabled.

The mechanical ventilation system, comprising driving means, i.e. gas supply selection valves 30, 32, 86A, 86B, and the expiration valve 40 controls the mechanical ventilation. The manual system, comprising the manual bag 50, as driving means, and the expiration valve 40 is used to control the manual ventilation.

In accordance with FIG. 1 the pressure level in the breathing circuit where controlled by controlling the flow of breathing gas through expiration valve 40 during both mechanical and manual ventilation.

In accordance with FIG. 5 the pressure level in the breathing circuit is controlled by controlling the flow of breathing gas through expiration valve 40 during manual ventilation, and by controlling the flow of driving gas through expiration valve 40 during mechanical ventilation.

In accordance with FIG. 6 the pressure level in the breathing circuit is controlled by controlling the flow of driving gas through expiration valve 40 during both mechanical and manual ventilation.

Although modifications and changes may be suggested by those skilled in the art, it is the intention of the inventors to embody within the patent warranted heron all changes and modifications as reasonably and properly come within the scope of their contribution to the art.

We claim as our invention:

1. A breathing apparatus for ventilating the lungs of a patient with breathing gas, comprising:
    a breathing circuit configured for interaction with a respirating subject;
    a mechanical ventilation system in communication with said breathing circuit to supply breathing gas to, and to receive exhaled gas from, the respirating patient, to satisfy mechanical ventilation mode requirements in a mechanical ventilation mode;
    a manual ventilation system configured to interact with the respirating subject to satisfy manual ventilation mode requirements in a manual ventilation mode, said manual ventilation system comprising a manually operable ventilation bag;
    a manual ventilation valve operable to place said manual ventilation system in communication with said breathing circuit to enable manual ventilation of breathing gas in said breathing circuit in said manual ventilation mode with manual operation of said ventilation bag;
    a pressure sensor that detects a pressure level, as a detected pressure level, in the breathing circuit;
    a control unit provided with said detected pressure level;
    an electronically controlled valve operated by said control unit dependent on said detected pressure level;
    said control unit being configured to operate said electronically controlled valve in said mechanical ventilation mode by adjusting the pressure level in the breathing circuit according to a first set of predetermined control rules adapted to said mechanical ventilation mode requirements, and to operate said electronically controlled valve in said manual ventilation mode by adjusting the pressure level in the breathing circuit according to a second set of predetermined control rules adapted to said manual ventilation mode requirements;
    said control unit being configured to operate said electronically controlled valve according to said second set of predetermined rules to at least, as a requirement among said manual ventilation mode requirements, prevent an overpressure in said breathing circuit that causes said respirating patient to resist manual ventilation in said manual ventilation mode; and
    said control unit being configured to operate said electronically controlled valve according to said first set of predetermined control rules as an expiration valve to, as requirements among said mechanical ventilation mode requirements, at least maintain said pressure level in the breathing circuit at a predetermined minimum pressure level, and enable a predetermined maximum pressure level in said breathing circuit in response to a detected predetermined pattern, selected from the group consisting of a pattern of said pressure level in said breathing circuit and a pattern of flow characteristics in said breathing circuit.

2. A breathing apparatus as claimed in claim 1 wherein said pattern is said pattern of pressure level, and wherein said pattern of pressure level comprises an increase in said pressure level corresponding to a predetermined pressure increase rate.

3. A breathing apparatus as claimed in claim 1 wherein said second set of predetermined control rules cause said expiration valve to operate to allow a predetermined maximum pressure level in said breathing circuit in response to said detected predetermined pattern in said breathing circuit.

4. A breathing apparatus as claimed in claim 1 wherein said pattern is a first pattern, and wherein said second set of predetermined control rules causes said expiration valve to operate to attain a predetermined standby pressure level in response to a detected predetermined second pattern selected from the group consisting of a pattern of said pressure level in said breathing circuit and a pattern of flow characteristics in said breathing circuit.

5. A breathing apparatus as claimed in claim 1 wherein said predetermined second pattern is a pattern of pressure level, and comprises a decrease in said pressure level corresponding to a predetermined pressure decrease rate.

6. A breathing apparatus as claimed in claim 5 wherein said second set of predetermined control rules causes said expiration valve to operate to allow a predetermined minimum pressure level in said breathing circuit in response to said detected predetermined first pattern.

7. A breathing apparatus as claimed in claim 1 wherein said second set of predetermined control rules causes said expiration valve to operate to enable a predetermined first pressure level in said breathing circuit in response to said detected predetermined pattern.

8. A breathing apparatus as claimed in claim 7 wherein said predetermined pattern is a predetermined first pattern, and wherein said second set of predetermined control rules causes said expiration valve to operate to attain a second pressure level in response to a detected predetermined second pattern selected from the group consisting of a pattern of said pressure level in said breathing circuit and a pattern flow characteristics in said breathing circuit.

9. A breathing apparatus as claimed in claim 8 wherein said second set of predetermined control rules causes said expiration valve to enable pressure variations in said breathing circuit around at least one of said first pressure level and said second pressure level within a predetermined pressure variation range that has upper and lower range values that, when exceeded allow spontaneous respiration by said respirating subject.

10. A breathing apparatus as claimed in claim 1 wherein said second set of predetermined control rules causes said expiration valve to operate to allow a predetermined maximum pressure level in the breathing circuit in response to a command signal received from a command signal input source.

11. A breathing apparatus as claimed in claim 1 wherein said second set of predetermined control rules causes said expiration valve to operate to enable predetermined pressure characteristics that depend on at least one of a detected pressure in said breathing circuit and a detected flow characteristic in said breathing circuit, in response to a command signal received from a command signal input source.

12. A breathing apparatus as claimed in claim 11 wherein said predetermined pressure characteristics represent pressure characteristics of Berner valve.

13. A breathing apparatus as claimed in claim 1 wherein said predetermined pressure characteristics represent pressure characteristics of APL valve.

14. A breathing apparatus as claimed in claim 1 wherein said first set of predetermined control rules trigger a change from said mechanical ventilation mode to said manual ventilation mode in response to said detected predetermined pattern.

15. A breathing apparatus as claimed in claim 1 wherein said predetermined pattern is a predetermined first pattern, and wherein said second set of predetermined control rules trigger a change from said manual ventilation mode to said mechanical ventilation mode in response to a detected predetermined second pattern, said predetermined second pattern comprising pressure characteristics in said breathing circuit.

16. A non-transitory, computer-readable data storage medium encoded with programming instructions for operating control unit of a breathing-assist device, said breathing-assist device comprising a breathing circuit configured for interaction with a respirating subject, a mechanical ventilation system in communication with said breathing circuit to supply breathing gas to, and to receive exhaled gas from, the respirating patient, to satisfy mechanical ventilation mode requirements in a mechanical ventilation mode, a manual ventilation system configured to interact with the respirating subject to satisfy manual ventilation mode requirements in a manual ventilation mode, said manual ventilation system comprising a manually operable ventilation bag, a manual ventilation valve operable to place said manual ventilation system in communication with said breathing circuit to enable manual ventilation of breathing gas in said breathing circuit in said manual ventilation mode with manual operation of said ventilation bag, a pressure sensor that detects a pressure level in the breathing circuit, and an electronically controlled valve operated by said control unit dependent on said detected pressure level, said programming instructions causing said control unit to:

operate said electronically controlled valve in said mechanical ventilation mode by adjusting the pressure level in the breathing circuit dependent on a first set of predetermined control rules, embodied in said programming instructions, adapted to said mechanical ventilation mode requirements, and to operate said electronically controlled valve in said manual ventilation mode by adjusting the pressure level in the breathing circuit according to a second set of predetermined control rules, embodied in said programming instructions, adapted to said manual ventilation mode requirements;

said second set of predetermined rules causing said control unit to operate said electronically controlled valve to at least, as a requirement among said manual ventilation mode requirements, prevent an overpressure in said breathing circuit that causes said respirating subject to resist manual ventilation in said manual ventilation mode; and said first set of predetermined control rules causing said control unit to operate said electronically controlled valve as an expiration valve to, as requirements among said mechanical ventilation mode requirements, at least maintain said pressure level in the breathing circuit at a predetermined minimum pressure level, and enable a predetermined maximum pressure level in said breathing circuit in response to a detected predetermined pattern, selected from the group consisting of a pattern of said pressure level in said breathing circuit and a pattern of flow characteristics in said breathing circuit.

17. A method for operating a breathing apparatus, comprising a breathing circuit configured for interaction with a respirating subject, a mechanical ventilation system in communication with said breathing circuit to supply breathing gas to, and to receive exhaled gas from, the respirating patient, to satisfy mechanical ventilation mode requirements in a mechanical ventilation mode, a manual ventilation system configured to interact with the respirating subject to satisfy manual ventilation mode requirements in a manual ventilation mode, said manual ventilation system comprising a manually operable ventilation bag, a manual ventilation valve operable to place said manual ventilation system in communication with said breathing circuit to enable manual ventilation of breathing gas in said breathing circuit by manual operation of said ventilation bag, a pressure sensor that detects a pressure level in the breathing circuit, a control unit provided with said detected pressure level, and an electronically controlled valve operated by said control unit dependent on said detected pressure level, said method comprising the steps of:

from said control unit, operating said electronically controlled valve in said mechanical ventilation mode by adjusting the pressure level in the breathing circuit dependent on a first set of predetermined control rules adapted to said mechanical ventilation mode requirements, and operating said electronically controlled valve in said manual ventilation mode by adjusting the pressure level in the breathing circuit according to a second set of predetermined control rules adapted to said manual ventilation mode requirements;

from said control unit, operating said electronically controllable valve according to said second set of predetermined rules to at least, as a requirement among said manual ventilation mode requirements, prevent an overpressure in said breathing circuit that causes said respirating subject to resist manual ventilation in said manual ventilation mode; and from said control unit, operating said electronically controlled valve according to said first set of predetermined control rules as an expiration valve to, as requirements among said mechanical ventilation mode requirements, at least maintain said pressure level in the breathing circuit and a predetermined minimum pressure level, and enable a predetermined maximum pressure level in said breathing circuit in response to a detected predetermined pattern, selected from the group consisting of a pattern of said pressure level in said breathing circuit and a pattern of flow characteristics in said breathing circuit.

18. A method as claimed in claim 17 comprising controlling said expiration valve during said manual ventilation mode to maintain the pressure level in the breathing circuit at a predetermined standby pressure level.

19. A method as claimed in claim 17 comprising controlling said expiration valve during said manual ventilation mode to set a predetermined manual ventilation pressure level in the breathing circuit in response to said detected predetermined pattern.

20. A method as claimed in claim 17 wherein said pattern is said pattern of pressure level, and using said pattern of pressure level to increase in said pressure level corresponding to a predetermined pressure increase rate.

21. A method as claimed in claim 17 comprising using said second set of predetermined control rules to cause said expiration valve to operate to allow a predetermined maximum pressure level in said breathing circuit in response to said detected predetermined pattern in said breathing circuit.

22. A method as claimed in claim 17 wherein said pattern is a first pattern, and comprising using said second set of predetermined control rules to cause said expiration valve to operate to attain a predetermined standby pressure level in response to a detected predetermined second pattern selected from the group consisting of a pattern of said pressure level in said breathing circuit and a pattern of flow characteristics in said breathing circuit.

23. A method as claimed in claim 22 wherein said predetermined second pattern is a pattern of pressure level, and comprising using said predetermined second pattern to cause a decrease in said pressure level corresponding to a predetermined pressure decrease rate.

24. A method as claimed in claim 23 comprising using said second set of predetermined control rules to cause said expiration valve to operate to allow a predetermined minimum pressure level in said breathing circuit in response to said detected predetermined first pattern.

25. A method as claimed in claim 17 comprising using said second set of predetermined control rules to cause said expiration valve to operate to enable a predetermined first pressure level in said breathing circuit in response to said detected predetermined pattern.

26. A method as claimed in claim 25 wherein said predetermined pattern is a predetermined first pattern, and comprising using said second set of predetermined control rules to cause said expiration valve to operate to attain a second pressure level in response to a detected predetermined second pattern selected from the group consisting of a pattern of said pressure level in said breathing circuit and a pattern flow characteristics in said breathing circuit.

27. A method as claimed in claim 25 comprising using wherein said second set of predetermined control rules to cause said expiration valve to enable pressure variations in said breathing circuit around at least one of said first pressure level and said second pressure level within a predetermined pressure variation range that has upper and lower range values that, when exceeded allow spontaneous respiration by said respirating subject.

28. A method as claimed in claim 17 comprising using said second set of predetermined control rules to cause said expiration valve to operate to allow a predetermined maximum pressure level in the breathing circuit in response to a command signal received from a command signal input source.

29. A method as claimed in claim 17 comprising using said second set of predetermined control rules to cause said expiration valve to operate to enable predetermined pressure characteristics that depend on at least one of a detected pressure in said breathing circuit and a detected flow characteristic in said breathing circuit, in response to a command signal received from a command signal input source.

30. A method as claimed in claim 17 comprising employing, as said predetermined pressure characteristics, characteristics that represent pressure characteristics of Berner valve.

31. A method as claimed in claim 17 comprising employing, as said predetermined pressure characteristics, characteristics that represent pressure characteristics of APL valve.

32. A method as claimed in claim 17 comprising using said first set of predetermined control rules to trigger a change from said mechanical ventilation mode to said manual ventilation mode in response to said detected predetermined pattern.

33. A method as claimed in claim 17 wherein said predetermined pattern is a predetermined first pattern, and comprising using said second set of predetermined control rules to trigger a change from said manual ventilation mode to said mechanical ventilation mode in response to a detected predetermined second pattern, said predetermined second pattern comprising pressure characteristics in said breathing circuit.

* * * * *